United States Patent [19]
Suekane

[11] Patent Number: 5,507,895
[45] Date of Patent: Apr. 16, 1996

[54] METHOD FOR MAKING DISPOSABLE DIAPERS

[75] Inventor: Makoto Suekane, Kawanoe, Japan

[73] Assignee: Uni-Charm Corporation, Ehime, Japan

[21] Appl. No.: 242,976

[22] Filed: May 16, 1994

[30] Foreign Application Priority Data

May 19, 1993 [JP] Japan ................................. 5-117346

[51] Int. Cl.$^6$ ........................................ A61F 13/15
[52] U.S. Cl. ................... 156/73.1; 156/204; 156/217; 156/227; 156/292; 156/308.4; 156/323; 156/324.4; 604/385.1
[58] Field of Search ................... 156/73.1, 73.4, 156/163, 164, 308.4, 323, 324.4, 292, 227, 217, 204; 604/358, 366, 370, 385.1; 2/400

[56] References Cited

U.S. PATENT DOCUMENTS

| | | |
|---|---|---|
| 3,924,626 | 12/1975 | Lee et al. . |
| 4,863,779 | 9/1989 | Daponte ..................... 428/152 |
| 5,064,489 | 11/1991 | Ujimoto et al. ................ 156/164 |

FOREIGN PATENT DOCUMENTS

| | | |
|---|---|---|
| 0234658 | 9/1987 | European Pat. Off. . |
| 0246858 | 11/1987 | European Pat. Off. . |
| 0531666 | 3/1993 | European Pat. Off. . |
| 5-15551 | 1/1993 | Japan . |
| 2170394 | 8/1986 | United Kingdom . |
| 2235125 | 2/1991 | United Kingdom . |
| 2257652 | 1/1993 | United Kingdom ............ 156/164 |
| 2268389 | 1/1994 | United Kingdom . |

Primary Examiner—Jeff H. Aftergut
Attorney, Agent, or Firm—Lowe, Price, LeBlanc & Becker

[57] ABSTRACT

To obtain a disposable diaper having at its respective waist sides welded zones which provide smooth touch, herein disclosed a method for making a disposable diaper 1 comprising steps of putting wing-like portions 21, 22 provided on front and rear bodies 5, 6 of the diaper 1 one upon another with a topsheet 2 facing inward, and welding these wing-like portions together under heat and pressure. In each wing-like portion 21, 22, a piece of sheet member is attached to at least one of the top- and backsheets 2, 3 so as to form an extension thereof and provide thereby the backsheet of said portion having a melting point higher than a melting point of the topside sheet member.

3 Claims, 4 Drawing Sheets

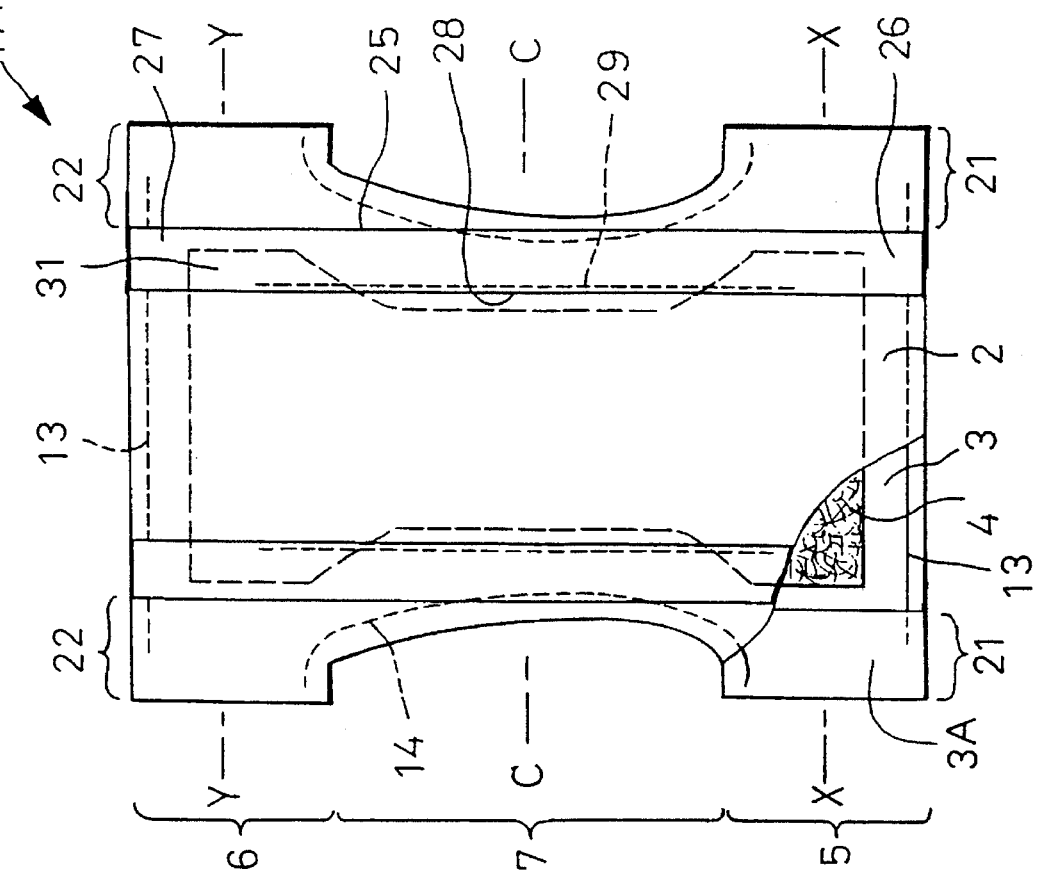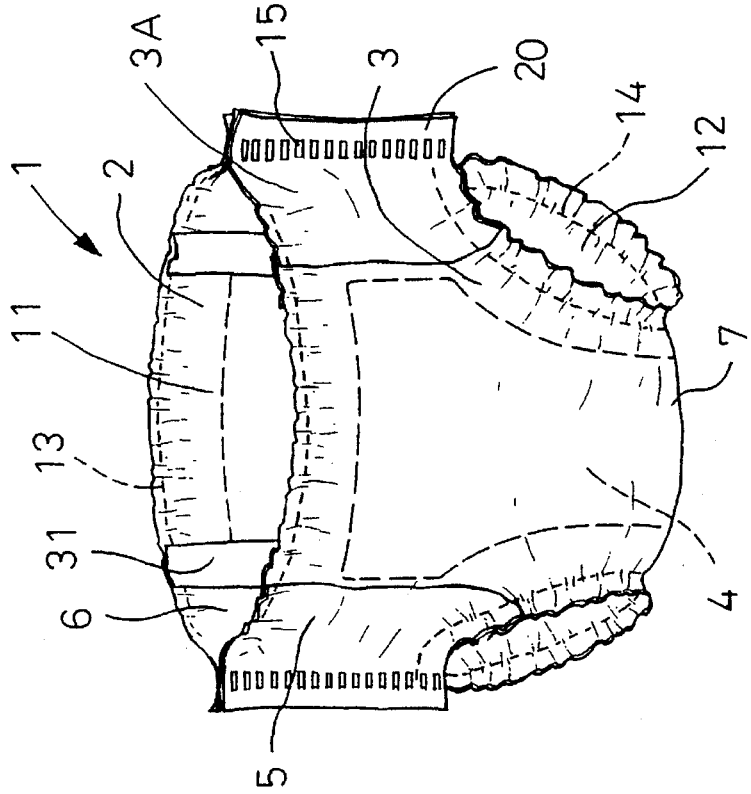

METHOD FOR MAKING DISPOSABLE DIAPERS

BACKGROUND OF THE INVENTION

The present invention relates to a method for making a disposable diaper with each of laterally opposite sides of a waist being welded.

One example of a pant type of disposable diapers is disclosed in Japanese Patent Application Disclosure No. 199315551, according to which a diaper comprising a topsheet, a backsheet, and a liquid-absorbent core sandwiched therebetween is folded up along a transverse center line passing through a crotch zone to lay front and rear bodies one upon another, and the top- and backsheets are ultrasonically welded together along laterally opposite side edges at its waist level to obtain a pant type configuration. The top- and backsheets may be prepared, for example, from nonwoven fabric of thermoplastic synthetic resin, both of which sheets can be molten together by ultrasonic treatment.

If the same kinds of nonwoven fabrics are used for the top- and backsheets in said Disclosure and molten at the same temperature to exhibit viscosities appropriate for welding, the welded top- and backsheets at the temperature may present a smoothly finished appearance. However, if the topsheet prepared from nonwoven fabric of polypropylene having a relatively high melting point is attached to the backsheet prepared from a polyethylene sheet having a relatively low melting point, the backsheet is molten earlier than the topsheet when the basic diaper is folded up like the joined hands and subjected to an ultrasonic welder. In consequence, the polyethylene of the backsheet may be molten to an excessively low viscosity and stick to a horn which has been pressed against the backsheet. The polyethylene sheet which has once sticked to the horn has, after cooled, a roughened surface giving a wearer of the diaper skin itchy stimulus as well as uncomfortable feel and a bad aesthetic appearance of the diaper. If a bit of the polyethylene sheet remains sticking to the horn, no accurate clearance can be assured between the horn and the anvil of the welder during the next welding cycle, making a continuous welding difficult.

Accordingly, it is a principal object of the invention to solve problems accompanying said prior art by preparing a backsheet in diaper's wing-like portions from a sheet having a melting point higher than a melting point of a topsheet thereof.

SUMMARY OF THE INVENTION

The object set forth above is achieved, according to the invention, by a method for making a disposable diaper generally comprising steps of assembling a liquid-permeable topsheet, a liquid-impermeable backsheet and a liquid-absorbent core sandwiched between these sheets into a basic configuration of a disposable diaper, putting wing-like portions of front and rear bodies of the diaper outwardly extending from laterally opposite side edges of said core one upon another like joined hands and welding said wing-like portions together under heat and pressure to form laterally opposite side portions of a waist levels of said front and rear bodies, said method further comprising steps of attaching a sheet to at least one of top- and backsheets in each wing-like portion so as to form an extension thereof and to provide the backsheet of said wing-like portions having a melting point higher than a melting point of the topsheet of said wing-like portions along each waist side, and welding these top- and backsheets together.

According to the method as has been described above, heating/pressing means such as an ultrasonic horn or a heating element of a desired shape is pressed against sheet portions to be welded together to form laterally opposite side edges of a waist of the diaper. A sheet having a relatively higher melting point is brought in contact with the heating/pressing means so as to prevent the topsheet, even if molten, from sticking to the heating/pressing means.

BRIEF DESCRIPTION OF THE DRAWINGS

The pants type disposable diaper made by the method of the invention will be described more in details with reference to the accompanying drawings, in which:

FIG. 1 is a perspective view of a pants type disposable diaper;

FIG. 2 is a plan view of the diaper as unfolded:

PREFERRED EMBODIMENTS OF THE INVENTION

Figure 3:
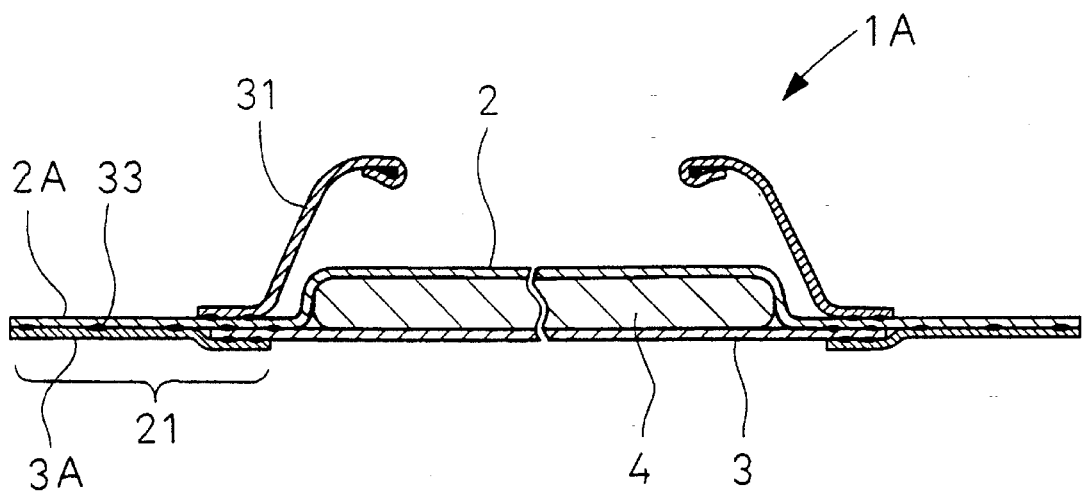
FIG. 3 is a partial sectional view taken along a line X—X in FIG. 2.

FIG. 1 is a perspective view showing a pants type disposable diaper 1 obtained by the method of the invention. The diaper 1 comprises a liquid-permeable topsheet 2 prepared from melt-bond nonwoven fabric of polypropylene fibre, a liquid-impermeable backsheet 3 prepared from polyethylene sheet, and a liquid-absorbent core 4 sandwiched between these sheets 2, 3. The diaper 1 is also generally configured by a front body 5, a rear body 6, and a crotch zone 7. The front and rear bodies 5, 6, are laid one on top of another with the topsheet 2 facing inward and welded together by an ultrasonic intermittent weld line vertically extending along each lateral side of the waist of the diaper 1. A portion of the backsheet 3 extending outward from laterally opposite side edges of the liquid-absorbent core 4 defines wing-like portions 21, 22 of the front and rear bodies 5, 6 as will be described more in detail and sheet members 3A attached to these wing-like portions 21, 22 comprise polypropylene sheets.

FIG. 2 is a plan view of the diaper 1A prior to said welding as unfolded (extended) longitudinally of the front and rear bodies 5, 6 and partially broken away. In the diaper 1A, portions of the front and rear bodies 5, 6 extending outward from lateral side edges of the liquid-absorbent core 4 define the wing-like portions 21, 22 of the front and rear bodies 5, 6, as has previously been mentioned. In these wing-like portions 21, 22, the sheet members 3A made of polypropylene sheets having a melting point higher than a melting point of the topsheet 2 are attached to side edges of the backsheet 3. On laterally opposite sides of the diaper 1A, there are provided a pair of flaps 31 longitudinally extending on the topsheet 2. Each flap 31 is attached to the topsheet 2 along its outer edge 25 as well as its longitudinally opposite ends 26, 27 so that its inner edge 28 can be raised from the top surface of the topsheet 2 under the effect of an elastic member 29 attached in a stretched condition to the inner edge 28.

FIG. 3 is a partial sectional view of the wing-like portion 21 taken along a line X—X in FIG. 2. The wing-like portion 21 comprises a sheet member 2A on the side of the topsheet 2 and the sheet member 3A. Referring to FIG. 3, the sheet member 3A comprises a piece of polypropylene sheet attached to the backsheet 3. In the wing-like portion 21, the topsheet 2 and the backsheet 3, on one hand, and the sheet member 2A and the sheet member 3A, on the other hand, are attached together, respectively, by means of hot melt adhesive 33. It should be understood here that a sectional view of the wing-like portion 22 taken along a line Y—Y in FIG. 2 is substantially same as FIG. 3 and therefore will not be described.

Figure 4:
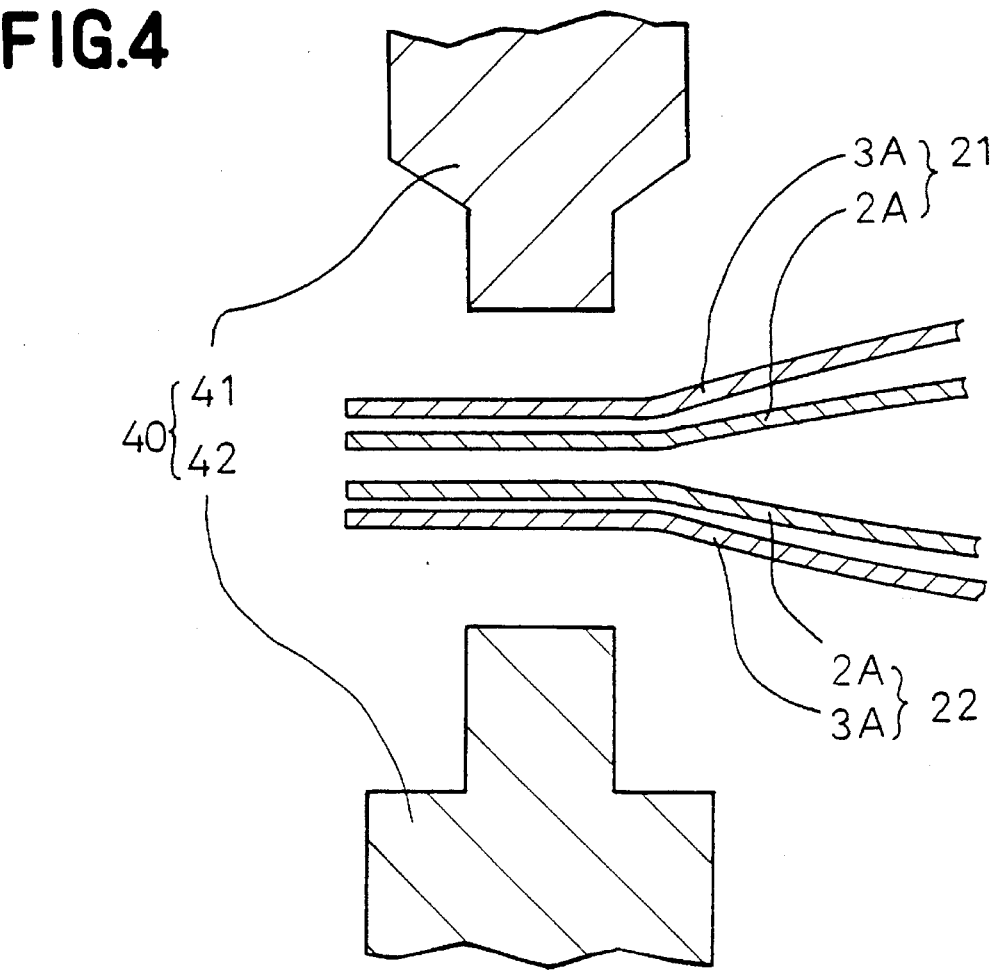
FIG. 4 is a schematic diagram illustrating an ultrasonic treatment.

FIG. 4 is a schematic side view illustrating a manner in which the diaper 1A is folded along a center line C—C inwardly and the wing-like portions 21, 22 of the front and rear bodies 5, 6 put together like joined hands are welded together by means of an ultrasonic welder 40. The welder 40 may be of a conventional type and comprises a horn 41 connected to an ultrasonic oscillator (not shown) and a stationary anvil 42, between which the wing-like portions 21, 22 are held and welded together so as to form a welded zone 15 (FIG. 1) being conformable to a shape of the horn 41 at its forward end.

Figure 5A:
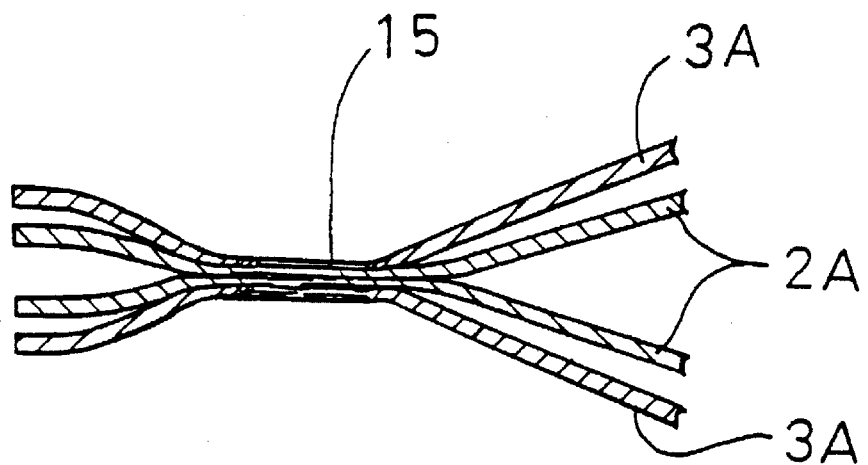
FIG. 5A and 5B are sectional views of welded zones presenting different configurations.
Figure 5B:
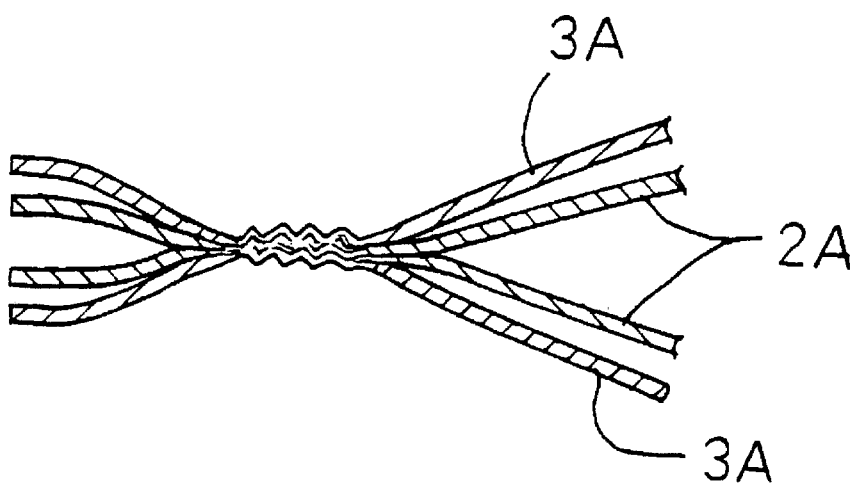

FIGS. 5A and 5B are schematic sectional views of the welded zones 15, wherein FIG. 5A illustrates the weld zone 15 obtained by subjecting the diaper 1 of FIG. 4 to an ultrasonic treatment and FIG. 5B illustrates, in comparison with the method of the invention, the case in which the topside sheet member 2A and the backside sheet member 3A of the wing-like portions 21, 22 are made of polypropylene nonwoven fabric and polyethylene sheet, respectively. In the case illustrated by FIG. 5A, decrease of polypropylene viscosity is not significant and welding occurs in a rather highly viscous molten state, so a mark pressed by the horn 41 on the welded zone 15 is round, resulting in a smooth finish giving no stimulus to the wearer's skin. In the case illustrated by FIG. 5B, on the other hand, when it is desired to weld the mutually opposing portions of inner polypropylene nonwoven fabric together, the outer polyethylene sheet is molten earlier to an excessively low viscosity and readily sticks to the horn 41 and the anvil 42. After cooled, the welded zone 15 presents rough surface which may give an itchy stimulus to the wearer's skin.

Figure 6A:
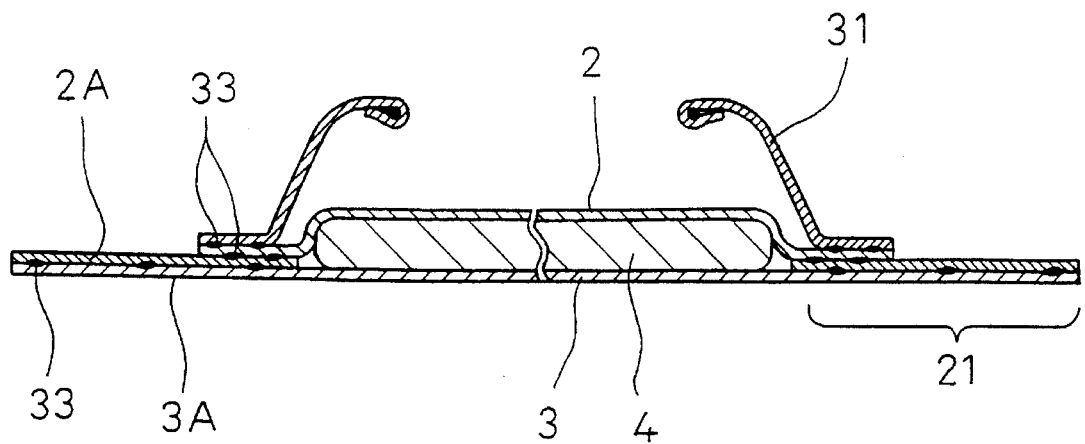
FIG. 6A, 6B and 6C are views similar to FIG. 3 showing different configurations.
Figure 6B:
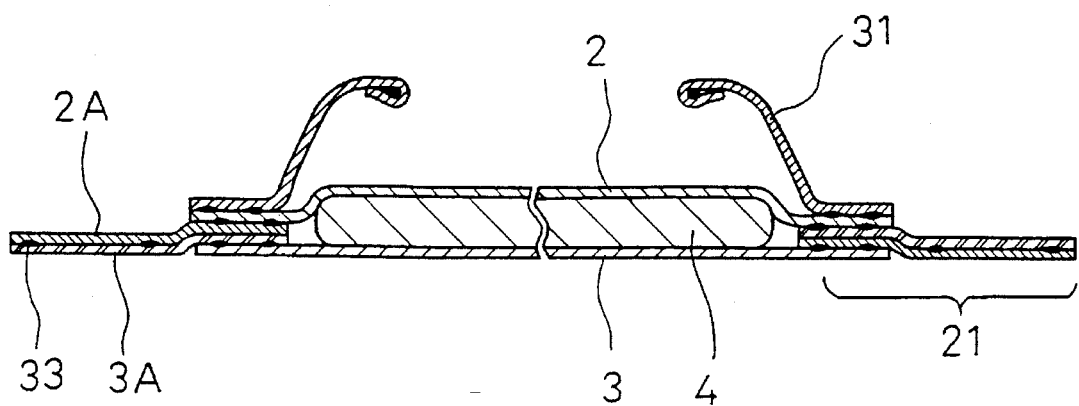
Figure 6C:
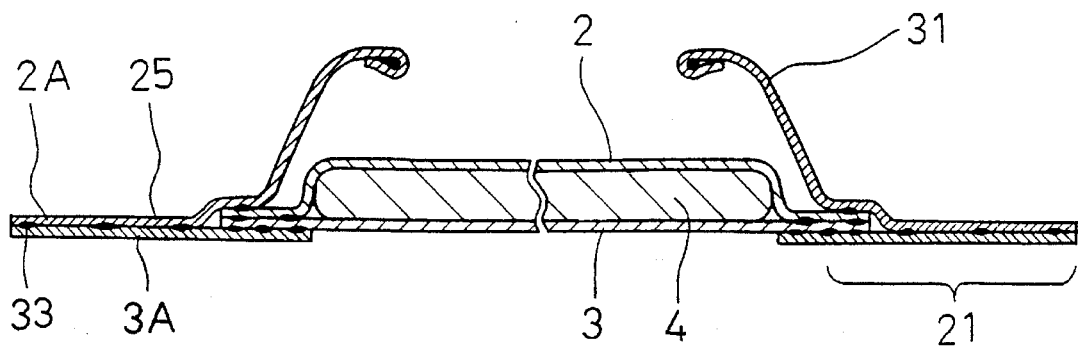

FIGS. 6A, 6B and 6C are partial sectional views showing configurations different from one another and different from the configuration shown by FIG. 3. In the case illustrated by FIG. 6A, the topsheet 2 is formed by melt-bond nonwoven fabric of polypropylene and the backsheet 3 is formed by a polyethylene sheet. In the wing-like portion 21, the topside sheet member 2A comprises a polyethylene sheet attached to the topsheet 2 by means of hot melt adhesive 33 so as to form an extension of the topsheet 2 and the backside sheet member 3A is formed by an extension of the backsheet 3, wherein the topside and backside sheet members 2A, 3A have the same melting point. In the case illustrated by FIG. 6B, the topside sheet member 2A comprising a polyethylene sheet is bonded to the topsheet 2 made of nonwoven fabric containing 60 weight % or higher of PET fibre and the backside sheet member 3A comprising a polypropylene sheet is attached to the backsheet 3 made of a polyethylene sheet. Finally, in the case illustrated by FIG. 6C, the outer side portion 25 of the flap 31 prepared from melt-bond nonwoven fabric of polypropylene is attached to the side edge of the topsheet 2 formed by the same nonwoven fabric as the flap 31. Said outer side portion 25 of the flap 31 is dimensioned sufficiently wide to form the topside sheet member 2A, and the backside sheet member 3A comprising a polypropylene sheet is attached to the backsheet 3 comprising a polyethylene sheet.

It is possible without departing from the scope of the invention to form each of the topside sheet member 2A and the backside sheet member 3A from a mixture of fibres having different melting points. The differential melting point in each sheet member should be understood as the differential melting point between the composing fibres totally occupying 60 weight % or higher of the sheet.

The melting point of the backside sheet member 3A should be equal to or higher than the melting point of the topside sheet member 2A and preferably higher than the latter in order to facilitate formation of a desirably shallow and small mark which will be made by the heating/pressing means.

When nonwoven fabric composed of polypropylene is used to prepare the topsheet 2 and the topside sheet member as in the diaper 1 illustrated as an embodiment of the invention, polypropylene will make the nonwoven fabric cushiony, depending on fineness as well as density, and give the wearer comfortable feel when the diaper 1 is put on the wearer's body. Use of the polyethylene sheet as the backsheet 3 will allow this relatively inexpensive sheet to provide comfortable soft touch.

While it is also conceivable to replace the method of the invention by a method comprising steps of the topside and backside sheets 2A, 3A are formed by extensions of the top- and backsheets 2, 3 and a covering sheet having a relatively high melting point is placed upon and welded with the backside sheet member 3A, such method is disadvantageous in that the number of sheets on the lateral sides of the waist unacceptably increases and may result in uncomfortably hard touch.

According to the method of the invention, the backside sheet member is not sufficiently melting to stick to the heating/pressing means such as the ultrasonic horn even under a condition of temperature at which the topside sheet member are sufficiently molten to be welded with each other, since the backside sheet member has a melting point higher than a melting point of the topside sheet member. In this manner, the invention solves the problem left by the prior art behind unsolved such that the welded zone presents, after cooled, rough surface which may give the wearer's skin an itchy stimulus and/or spoil an aesthetic appearance of the diaper.

What is claimed is:

1. A method for making a disposable diaper generally comprising steps of assembling a liquid-permeable topsheet, a liquid-impermeable backsheet and a liquid-absorbent core sandwiched between these sheets into a configuration of disposable diaper, putting wing-like portions of front and rear bodies of the diaper outwardly extending from laterally opposite side edges of said core one upon another and welding said wing-like portions together under heat and pressure to form laterally opposite side portions at waist levels of said front and rear bodies, said method further comprising steps of:

attaching a sheet to at least one of top- and backsheets in each wing-like portion so as to form an extension thereof and provide thereby the backsheet of said portion having a melting point higher than a melting point of the topsheet of said portion, and welding said top- and backsheets together along each waist side of the diaper.

2. The method of claim 1 wherein the topsheet has a melting point higher than that of the backsheet, a sheet which is attached to said topsheet in said wing-like portion having a melting point lower than that of said backsheet.

3. The method of claim 1 wherein the topsheet has a melting point higher than that of the backsheet, a sheet which is attached to said backsheet in said wing-like portion having a melting point higher than that of said topsheet.

\* \* \* \* \*